(12) United States Patent
Engblom et al.

(10) Patent No.: US 8,217,062 B2
(45) Date of Patent: Jul. 10, 2012

(54) TOPICAL COMPOSITION COMPRISING A DIHYDROPYRIDINE CALCIUM ANTAGONIST

(75) Inventors: Johan Engblom, Lund (SE); Birgitta Svensson, Limhamm (SE); Anette Abrahamsson, Malmö (SE); Åke Lindahl, Malmö (SE)

(73) Assignee: Moberg Derma AB, Solna (SE)

( * ) Notice: Subject to any disclaimer, the term of this patent is extended or adjusted under 35 U.S.C. 154(b) by 0 days.

(21) Appl. No.: 12/439,100

(22) PCT Filed: Aug. 31, 2007

(86) PCT No.: PCT/SE2007/000758
§ 371 (c)(1),
(2), (4) Date: Jul. 31, 2009

(87) PCT Pub. No.: WO2008/026984
PCT Pub. Date: Mar. 6, 2008

(65) Prior Publication Data
US 2010/0010052 A1    Jan. 14, 2010

(30) Foreign Application Priority Data
Sep. 1, 2006  (SE) ...................................... 0601806

(51) Int. Cl.
*C07D 211/90*  (2006.01)
(52) U.S. Cl. ........................................ 514/356; 514/947
(58) Field of Classification Search ......................... None
See application file for complete search history.

(56) References Cited

U.S. PATENT DOCUMENTS
| | | | |
|---|---|---|---|
| 6,680,334 B2 | 1/2004 | Bentham et al. | |
| 2004/0028752 A1 | 2/2004 | Kamm et al. | |
| 2008/0200533 A1* | 8/2008 | Krishnan | 514/423 |

FOREIGN PATENT DOCUMENTS
| | | |
|---|---|---|
| EP | 1 250 927 A2 | 10/2002 |
| WO | WO-94/21271 A1 | 9/1994 |
| WO | WO 9421271 A1 * | 9/1994 |
| WO | WO 98/36733 A2 | 8/1998 |
| WO | WO 9836733 A2 * | 8/1998 |

OTHER PUBLICATIONS

Katsinelos et al., "Topical 0.5% nifedipine vs. lateral internal sphincterotomy for the treatment of chronic anal fissure: long-term follow-up", Int J Colorectal Dis, 2006, vol. 21, pp. 179-183.

Gennaro., Remington: The Science and Practice of Pharmacy, 20th Edition, pp. 845-851, 2000, ISBN:0-683-306472.

Aungst B. J. et al., "Enhancement of naloxone penetration through human skin in vitro using fatty acids, fatty alcohols, surfactants, sulfoxides and amides", International Journal of Pharmaceutics, Nov. 1, 1986, vol. 33, No. 1-3, pp. 225-234 Elsevier Science Publishers B.V., NL, XP023724411.

Santus, G. C. et al. "Transdermal enhancer patent literature", Journal of Controlled Release, May 27, 1993, vol. 25, No. 1-2, pp. 1-20, Elsevier Science Publishers B.V., Amsterdam, NL, XP025526719.

T.A. Cook et al., "Review article: the pharmacology of the internal anal sphincter and new treatments of ano-rectal disorders", Aliment Pharmacol Ther, Blackwell Science Ltd., 2001, vol. 15, pp. 887-898.

\* cited by examiner

*Primary Examiner* — Sreeni Padmanabhan
*Assistant Examiner* — Svetlana M Ivanova
(74) *Attorney, Agent, or Firm* — Jeffrey S. Melcher; Manelli Selter PLLC

(57) ABSTRACT

A topical composition comprising a dihydropyridine calcium antagonist, a stiffening agent and a release modifier. The stiffening agent comprises a fatty alcohol, a fatty acid sorbitane ester, or a fatty acid glycerol ester, having a hydrocarbon chain containing 12 to 22 carbon atoms and having a melting point of about 45 to 750° C. The release modifier comprises a fatty alcohol, a fatty alcohol glycol ether, a fatty acid alkyl ester, a fatty acid glycerol ester, or a fatty acid sorbitane ester, having a hydrocarbon chain containing 12 to 18 carbon atoms and having a melting point of about −10 to 400° C. Use of such a composition for the treatment and/or prophylaxis of a dermal or mucosal disorder, preferably an anorectal disorder associated with high anal pressure or anal sphincter spasm.

18 Claims, No Drawings

TOPICAL COMPOSITION COMPRISING A DIHYDROPYRIDINE CALCIUM ANTAGONIST

CROSS-REFERENCE TO RELATED APPLICATIONS

This application is a national stage entry under 35 U.S.C. 371 of International Application No. PCT/SE2007/000758, filed 31 Aug. 2007, designating the United States. This application claims foreign priority under 35 U.S.C. 119 and 365 to Swedish Patent Application No. 0601806-3, filed 1 Sep. 2006. The complete contents of these applications are incorporated herein by reference.

TECHNICAL FIELD

The present invention relates to a topical composition comprising as an active ingredient a dihydropyridine calcium antagonist, or a prodrug thereof, and a pharmaceutically acceptable carrier, to the use of such a composition for the manufacture of a medicament for the treatment or prophylaxis of a dermal or mucosal disorder, preferably an anorectal disorder, and to a method of treating or preventing such disorder.

BACKGROUND ART

Anal fissure is an ulcer in the squamous epithelium of the anus just distal to the mucocutaneous junction and usually in the posterior midline. It typically causes pain during defecation and for one to two hours afterwards. Even if anal fissures are rather common, pathogenesis and etiology are still incompletely understood. Nevertheless, there is evidence in the literature that anal fissures are connected with high resting anal pressure. A mucosal ischemia, in 90% of the cases in the posterior midline, may be produced if the high pressure in the anal canal exceeds the capillary pressure. Permanent elevated resting pressure is thought to impair the intrasphincteric blood flow. This reduction in mucosal blood flow leads to microcirculatory disturbance and poor healing tendency.

The fissures can be separated into acute and chronic anal fissures. A fissure has been defined as acute if it has been present for less than six weeks and chronic if it has been present for more than six weeks. Furthermore, anal fissures are claimed to affect men and women equally. Spontaneous healing occurs in 50% of the acute anal fissures in adults with or without treatment. High fibre diet is recommended and pain relief (topical anaesthetics) is reported to be effective on acute anal fissures in some people. However, a significant number of patients develop chronic anal fissures.

Surgical intervention via lateral sphincterotomy is still described as gold standard for curing chronic anal fissures. The healing rate is reported to be 94-100%. However, since sphincterotomy is associated with asymmetry of the anal canal and irreversible sphincter damage, there is a concern about long term results and fecal incontinence. The prevalence of incontinence of feces or flatus is as high as 38% after surgery. It has also been stated that there is a risk for some degree of incontinence in up to 30% of the patients that underwent sphincterotomy. This concern has over the last years led to considerations to develop medical treatments for anal fissures that temporarily and reversibly reduce anal pressure, based on the underlying pharmacology.

Recent research has revealed the basic pharmacology of the internal anal sphincter. Cook T. A. et al. provide in "The pharmacology of the internal anal sphincter and new treatments of ano-rectal disorders", *Aliment Pharmacol Ther* 2001:15:887-898, a detailed overview on this aspect, which indicates potential starting points for medical treatment. The calcium concentration is considered to be the key factor for the tonus of the anal sphincter. The extracellular calcium concentration and the flux across the cell membranes through L-type calcium channels are important, as well as the calcium release from intracellular stores. Contraction is related to mechanisms that increase the intracellular calcium ion concentration above about $10^{-7}$ mol/l and relaxation to mechanisms causing a decrease in cytosolic calcium below this concentration.

Several compound classes have been evaluated over the last years as candidates for pharmacological treatment of anal fissures. These compound classes encompass NO donors, Botulinum toxin A, muscarinic agents, β-receptor agonists, α-antagonists and calcium antagonists, the calcium antagonists, and the dihydropyridines in particular, appearing to be the most promising alternative. Dihydropyridines are vasodilatory agents and are relatively smooth muscle selective.

US 2004/0028752 provides a method and composition for the treatment of an anorectal disorder and for controlling the pain associated therewith. The method comprises administering to a subject in need of such treatment therapeutically effective amounts of a calcium channel blocker either alone or together with a nitric oxide donor. In the Examples, topical application of a diltiazem hydrochloride cream is disclosed. The cream comprises 50% w/w dimethyl sulphoxide (DMSO).

For toxicological reasons, a medicament containing DMSO is undesirable. Thus, the prior art fails to provide a useful composition for the administration of a calcium antagonist for the treatment or prophylaxis of anal disorders.

SUMMARY OF THE INVENTION

An object of the present invention is to provide improved bioavailability of a calcium antagonist, or a prodrug thereof. Thus, it is an object of the present invention to provide improved drug release of a calcium antagonist, or a prodrug thereof, from a topical composition. It is also an object to provide improved drug penetration of a calcium antagonist, or a prodrug thereof, over biological membranes, such as skin or mucosa.

An object of the present invention is also to provide a therapeutically effective tissue concentration of a calcium antagonist, or a prodrug thereof, over a prolonged application interval.

Another object is to provide an alternative to prior art topical compositions for the release of a calcium antagonist, or a prodrug thereof, particularly to provide an alternative to such compositions containing toxic components.

Yet another object is to provide effective treatment or prophylaxis of anal disorders.

The above-mentioned objects as well as other objects of the invention, which can be gathered by a person skilled in the art after having studied the description below, are accomplished by a topical composition comprising as an active ingredient a dihydropyridine calcium antagonist, or a prodrug thereof, present to a substantial part in uncharged form and a pharmaceutically acceptable carrier comprising a stiffening agent and a release modifier, wherein the stiffening agent comprises a fatty alcohol, a fatty acid sorbitane ester, or a fatty acid glycerol ester, having a hydrocarbon chain containing 12 to 22 carbon atoms and having a melting point in pure state of about 45 to 75° C.;

the release modifier comprises a fatty alcohol, a fatty alcohol glycol ether, a fatty acid alkyl ester, a fatty acid glycerol ester, or a fatty acid sorbitane ester, having a hydrocarbon chain containing 12 to 18 carbon atoms and having a melting point in pure state of about −10 to 40° C.; and the stiffening agent and the release modifier are selected so that the number of carbon atoms contained in the hydrocarbon chain of the stiffening agent and the number of carbon atoms contained in the hydrocarbon chain of the release modifier differ by 0, 1, 2, 3, or 4.

Thus, in a composition according to the invention the dihydropyridine calcium antagonist, or the prodrug thereof, as an active ingredient, is present to a substantial part in uncharged form. The uncharged form has been found to penetrate biological membranes such as skin to a higher extent than, e.g., a salt form of the active ingredient.

The composition according to the invention comprises furthermore a pharmaceutically acceptable carrier particularly designed for release of the uncharged dihydropyridine calcium antagonist, or the prodrug thereof. Thus, in the carrier as defined above the stiffening agent and the release modifier have been found to interact to facilitate release of the active ingredient.

By the composition according to the invention improved bioavailability of the active ingredient is achieved and, moreover, in a composition free from toxic components.

The term "dihydropyridine calcium antagonist" as used herein refers to calcium antagonists (calcium channel blocking agents) based upon pyridine that have been semi-saturated with two hydrogen atoms replacing one double bond. Such calcium antagonists are substances that bind to and inhibit the voltage-gated calcium channel of skeletal muscle T junctional membranes, the principle molecular transducer of excitation-contraction coupling. In The Anatomical Therapeutic Chemical Classification System (ATCCS), used for the classification of drugs and controlled by the WHO Collaborating Centre for Drug Statistics Methodology, such compounds are classified in class C08CA (Selective calcium channel blockers with mainly vascular effects, dihydropyridine derivatives). Thus, ample guidance exists for a skilled man seeking to employ a dihydropyridine calcium antagonist in the present invention.

The term "prodrug" as used herein refers to a derivative of a drug, in this case a derivative of a dihydropyridine calcium antagonist, which must undergo chemical conversion by metabolic processes before becoming an active pharmacological agent. In the present invention, the dihydropyridine calcium antagonist as well as the prodrug thereof is present to a substantial part in uncharged form.

The term "to a substantial part" as used herein refers to about 10% by weight or more of the substance in question.

The term "hydrocarbon chain" as used herein refers to the hydrocarbon chain of the "fatty" or "fatty acid" moiety of a molecule. The number of carbon atoms in a hydrocarbon chain includes carbon atoms in chain branches, if occurring.

The term "melting point in pure state" as used herein refers to the melting point of a substance as determined by conventional means such as the use of melting point capillaries or differential scanning calorimetry. The term further refers, as is also conventional, to the melting point of the substance as such, not present in admixture with any substantial amounts of other substances. This, however, does not mean that the term "pure state" in the present application indicates that the substance must be 100% pure. The term "pure state", in the present application, refers to the purity of the substance as it is commercially available for pharmaceutical use. Accordingly, the "melting point in pure state" referred to in the present application relates to the melting point of the substance as it is commercially available for pharmaceutical use. Melting points of substances referred to herein are readily available to a skilled man by reference to handbooks and/or by routine measurements. Accordingly, a skilled man is able to select appropriate carrier components within the scope of the claims.

As known to a person skilled in the art, the melting point of lipids like fatty alcohols, fatty acids, fatty acid glycol esters and fatty acid glycerol esters is highly dependent on their molecular structure. The main work on thermotropic behaviour of these substances has been performed on free fatty acids, although the observations made are generally also valid for related alcohols, ethers and esters. Based on such dependencies, a skilled man is further advised regarding the selection of appropriate carrier components within the scope of the claims.

The term "the number of carbon atoms . . . differ by" as used herein refers to the difference in number of carbon atoms between the hydrocarbon chains of the respective carrier components. Accordingly, in the present invention the hydrocarbon chain of the stiffening agent may have 0, 1, 2, 3, or 4 more or fewer carbon atoms than the hydrocarbon chain of the release modifier. A difference of 0, 1, or 2 is preferred and a difference of 0 is more preferred. Hence, a skilled man is readily able to select a stiffening agent and a release modifier within the scope of the claims.

In the present invention, the dihydropyridine calcium antagonist, or the prodrug thereof, in uncharged form may be present in free base form.

The serum half life of the dihydropyridine calcium antagonist is relevant for the treatment of, e.g., anal fissures since in order to promote healing of the fissures the reduction of pressure of the sphincter should be maintained until a further dose has been applied. A serum half life exceeding about 8 hours, preferably exceeding about 12 hours, is desirable in view of the desirable dose interval. A sufficiently long half life can be achieved by amlodipine, felodipine, lacidipine, nitrendipine, or nisoldipine; preferably by amlodipine, felodipine, or nisoldipine; more preferably by amlodipine.

In the present invention, the dihydropyridine calcium antagonist, or the prodrug thereof, may be present in amount of up to 6% by weight, preferably about 0.1 to 3% by weight, based on the weight of the composition. The amount may be adapted the requirements for an indication to be treated or prevented.

In an embodiment of the present invention, the stiffening agent comprises a fatty alcohol, having a hydrocarbon chain containing 16 to 18 carbon atoms and having a melting point in pure state of about 45 to 65° C.

In another embodiment of the present invention, the stiffening agent is cetyl alcohol, stearyl alcohol, cetostearyl alcohol, eicosanol, docosanol, sorbitane monopalmitate, sorbitane monostearate, glyceryl monopalmitate, glyceryl monostearate, or glyceryl monopalmitostearate.

It has been found that a suitable stiffening agent is cetyl alcohol, stearyl alcohol, or cetostearyl alcohol; preferably stearyl alcohol.

A stiffening agent may be provided as such in a composition according to the invention. Alternatively, the stiffening agent may be provided as part of a component comprising further ingredients. As an example, cetomacrogol emulsifying wax (as defined in the British Pharmacopoeia) or emulsifying wax (as defined in the United States Pharmacopeia) are suitable sources of the stiffening agent, cetostearyl alcohol.

In a composition according to the invention, the stiffening agent may be present in an amount of about 10 to 30% by weight, based on the weight of the composition.

In an embodiment of the present invention, the release modifier comprises a fatty alcohol, or a fatty acid glycerol ester, having a hydrocarbon chain containing 12 to 18 carbon atoms and having a melting point in pure state of about −10 to 40° C.

In another embodiment of the present invention, the release modifier comprises a fatty alcohol, having a hydrocarbon chain containing 12 to 18 carbon atoms and having a melting point in pure state of about −10 to 40° C.

In another embodiment of the present invention, the release modifier is dodecanol, tetradecanol, palmitoyl alcohol, oleyl alcohol, linoleyl alcohol, polyoxyethylene lauryl ether, polyoxyethylene myristyl ether, polyoxyethylene cetyl ether, polyoxyethylene stearyl ether, sorbitane monolaurate, sorbitane monooleate, or glyceryl monooleate.

It has been found that a suitable release modifier is dodecanol, tetradecanol, palmitoyl alcohol, oleyl alcohol, linoleyl alcohol, or glyceryl monooleate. Alternatively, a suitable release modifier is dodecanol, tetradecanol, palmitoyl alcohol, oleyl alcohol, or linoleyl alcohol; preferably oleyl alcohol.

In a composition according to the invention, the release modifier may be present in an amount of up to about 20% by weight, preferably about 1 to 15% by weight, based on the weight of the composition.

It has been found that release of the dihydropyridine calcium antagonist, or the prodrug thereof, from a composition according to the invention may be further improved when a polar solvent miscible with both oil and water is present in the composition. Hence, one embodiment of the present invention relates to a composition as defined above further comprising a polar solvent having an octanol-water partition coefficient (P) of about $-1.5 < \log P < 0.5$, preferably about $-1 < \log P < 0$. The octanol-water partition coefficient is in general use for the characterisation of the miscibility properties of a solvent with oil and water, respectively. Thus, a skilled man is readily able to select a suitable polar solvent based on information about said coefficient.

Suitable polar solvents for use in the invention are diethanol amine, dipropylene glycol, diethylene glycol monoethyl ether, methyl ethyl ketone, 1-methyl-2-pyrrolidone, 1-propanol, 2-propanol, propylene glycol, or propylene carbonate, or a combination thereof; preferably diethylene glycol monoethyl ether, 1-methyl-2-pyrrolidone, propylene glycol, or propylene carbonate, or a combination thereof; more preferably propylene glycol.

In a composition according to the invention, the polar solvent is present in an amount of up to about 20% by weight, based on the weight of the composition. The amount of polar solvent is preferably about 7 to 17% by weight, more preferably about 10 to 14% by weight.

In order to modify the texture of the composition according to the invention, the composition may further comprise a petroleum fraction, such as petrolatum and/or mineral oil, preferably in an amount of about 15 to 75% by weight, based on the weight of the composition.

In an inventive composition comprising a petroleum fraction, it is appreciated that a portion of the release modifier may be present in said petroleum fraction. In a composition comprising a petroleum fraction the stiffening agent and the release modifier may be present in a weight ratio of about 10:1 to 1:1, preferably about 5:1 to 1.5:1.

The objects of the invention are also accomplished by use of a composition as defined above for the manufacture of a medicament for the treatment or prophylaxis of a dermal or mucosal disorder, preferably an anorectal disorder associated with high anal pressure or anal sphincter spasm.

The objects of the invention are also accomplished by a method of treating or preventing a dermal or mucosal disorder, preferably an anorectal disorder associated with high anal pressure or anal sphincter spasm, which comprises administering to a patient in need of such treatment or prevention a composition as defined above in a therapeutically effective amount.

The treatment or prophylaxis/prevention of such a disorder is particularly well achieved with the inventive composition, since it has outstanding release and penetration properties in respect of the dihydropyridine calcium antagonist, or the prodrug thereof, as an active ingredient.

Anorectal disorders associated with high anal pressure or anal sphincter spasm may be acute anal fissures, chronic anal fissures, or hemorrhoids.

The inventive composition is for topical application on skin or mucosa, such as in or around the anal canal.

DESCRIPTION OF PREFERRED EMBODIMENTS

In one embodiment, the inventive composition is present as a cream, sometimes referred to as an emulsion. Such cream comprises, in addition to the active ingredient, the stiffening agent and the release modifier, a polar solvent as described above, water or a substitute thereof, and a petroleum fraction.

In such cream, the stiffening agent may comprise a fatty alcohol, having a hydrocarbon chain containing 16 to 18 carbon atoms and having a melting point in pure state of about 45 to 65° C. Alternatively, the stiffening agent may be cetyl alcohol, stearyl alcohol, or cetostearyl alcohol, preferably stearyl alcohol.

In such cream, the release modifier may comprise a fatty alcohol, a fatty alcohol glycol ether, or a fatty acid sorbitane ester, having a hydrocarbon chain containing 12 to 18 carbon atoms and having a melting point in pure state of about −10 to 40° C. Alternatively, the release modifier may be dodecanol, tetradecanol, palmitoyl alcohol, oleyl alcohol, linoleyl alcohol, polyoxyethylene lauryl ether, polyoxyethylene myristyl ether, polyoxyethylene cetyl ether, polyoxyethylene stearyl ether, sorbitane monolaurate, sorbitane monooleate, or glyceryl monooleate, preferably oleyl alcohol.

In a preferred cream, the release modifier may comprise a fatty alcohol, having a hydrocarbon chain containing 12 to 18 carbon atoms and having a melting point in pure state of about −10 to 40° C. Alternatively, the release modifier may be dodecanol, tetradecanol, palmitoyl alcohol, oleyl alcohol, or linoleyl alcohol, preferably oleyl alcohol.

The release modifier may be present in the cream in an amount of about 1 to 12% by weight, preferably about 2 to 10% by weight, based on the weight of the composition.

In the cream, water or a substitute thereof is present. Suitable substitutes are glycerol or ethanol.

In the cream, the petroleum fraction, such as petrolatum, may be present in an amount of 15 to 40% by weight, based on the weight of the composition.

In another embodiment, the inventive composition is present as an ointment. Such ointment comprises, in addition to the active ingredient, the stiffening agent and the release modifier, a polar solvent as described above and a petroleum fraction.

In such ointment, the stiffening agent may comprise a fatty alcohol, having a hydrocarbon chain containing 16 to 18 carbon atoms and having a melting point in pure state of about 45 to 65° C. Alternatively, the stiffening agent may be cetyl alcohol, stearyl alcohol, or cetostearyl alcohol, preferably stearyl alcohol. Cetomacrogol emulsifying wax is a source of cetostearyl alcohol and thus a convenient way of providing a stiffening agent in the ointment.

In such ointment the release modifier may comprise a fatty alcohol, a fatty alcohol glycol ether, a fatty acid alkyl ester, a fatty acid glycerol ester, or a fatty acid sorbitane ester, having a hydrocarbon chain containing 12 to 18 carbon atoms and having a melting point in pure state of about −10 to 40° C. Alternatively, the release modifier may be dodecanol, tetradecanol, palmitoyl alcohol, oleyl alcohol, linoleyl alcohol, polyoxyethylene lauryl ether, polyoxyethylene myristyl ether, polyoxyethylene cetyl ether, polyoxyethylene stearyl ether, sorbitane monolaurate, sorbitane monooleate, or glyceryl monooleate, preferably oleyl alcohol.

In such ointment, the release modifier may comprise a fatty alcohol, a fatty alcohol glycol ether, or a fatty acid sorbitane ester, having a hydrocarbon chain containing 12 to 18 carbon atoms and having a melting point in pure state of about −10 to 40° C.

In a preferred ointment, the release modifier may be dodecanol, tetradecanol, palmitoyl alcohol, oleyl alcohol, or linoleyl alcohol; preferably oleyl alcohol.

The release modifier may be present in the ointment in an amount of about 5 to 15% by weight, preferably about 8 to 12% by weight, based on the weight of the composition.

In the ointment, the petroleum fraction, such as petrolatum and/or mineral oil, may be present in an amount of 50 to 75% by weight, based on the weight of the composition.

EXAMPLES

The following non-limiting examples will further illustrate the present invention.

Example 1

Comparative Example

One hydrophilic and one lipophilic ointment were manufactured containing a dihydropyridine calcium antagonist (amlodipine) (Compositions 1-2, Table 1a).

TABLE 1a

| Composition, % (w/w) | 1 | 2 |
|---|---|---|
| Amlodipine base | 2.0 | 0.5 |
| Polyethylene glycol 400 | 60.0 | — |
| Polyethylene glycol 3350 | 38.0 | — |
| Propylene glycol, PG | — | 5.0 |
| Sorbitan sesquioleate | — | 0.5 |
| White petroleum jelly | — | 94.0 |
| Total | 100.0 | 100.0 |

The compositions were tested for release rate in Franz cells, where the drug release over silicone membranes was determined at 37° C. (Table 1b).

TABLE 1b

|  | 1 | 2 |
|---|---|---|
| Cumulative amount, μg/cm² (6 h) | 8 | 8 |

Example 2

A series of related ointments where manufactured containing varying amounts of a biologically active agent (amlodipine), a release modifier (oleyl alcohol), a stiffening agent (cetostearyl alcohol as cetomacrogol emulsifying wax), a polar solvent (propylene glycol) and a petroleum fraction (petrolatum and paraffin oil) as texture modifier (Compositions 3-8, Table 2a).

TABLE 2a

| | Composition, % (w/w) | | | | | |
|---|---|---|---|---|---|---|
| | 3 | 4 | 5 | 6 | 7 | 8 |
| Amlodipine base | 2.0 | 2.0 | 2.0 | 2.0 | 2.0 | 4.0 |
| Petrolatum, white | 48.0 | 48.0 | 48.0 | 48.0 | 48.0 | 48.0 |
| Cetomacrogol emulsifying wax | 30.0 | 27.5 | 25.0 | 20.0 | 15.0 | 23.0 |
| Paraffin oil | 20.0 | 20.0 | 20.0 | 20.0 | 20.0 | 20.0 |
| Oleyl alcohol, OA | — | 2.5 | 5.0 | 10.0 | 15.0 | 5.0 |
| Total | 100.0 | 100.0 | 100.0 | 100.0 | 100.0 | 100.0 |

The compositions were tested for release rate in Franz cells, where the drug release over silicone membranes was determined at 37° C. (Table 2b).

TABLE 2b

| | 3 | 4 | 5 | 6 | 7 | 8 |
|---|---|---|---|---|---|---|
| Cumulative amount, μg/cm² (6 h) | 22 | 55 | 95 | 152 | 124 | 89 |

Compositions 3 to 7 illustrate the effect of the release modifier (here, oleyl alcohol). Composition 6, comprising an approximate ratio in stiffening agent to release modifier of 2:1, produced an optimum drug release from the vehicle. The drug release was improved seven-fold by addition of the release modifier (c.f. composition 3). Compositions 5 and 8 illustrate the effect of the drug content.

Example 3

A series of related creams were manufactured containing a biologically active agent (amlodipine), a release modifier (oleyl alcohol), a stiffening agent (stearyl alcohol), a polar solvent (propylene glycol), water and a petroleum fraction (petrolatum) as texture modifier, where the amount of release modifier was increased on the expense of the amount of stiffening agent (Compositions 9-16, Table 3a).

TABLE 3a

| | Composition, % (w/w) | | | | | | | |
|---|---|---|---|---|---|---|---|---|
| | 9 | 10 | 11 | 12 | 13 | 14 | 15 | 16 |
| Amlodipine base | 2.0 | 2.0 | 2.0 | 2.0 | 2.0 | 2.0 | 2.0 | 2.0 |
| Petrolatum, white | 25.0 | 25.0 | 25.0 | 25.0 | 25.0 | 25.0 | 25.0 | 25.0 |
| Tween 80 | 1.0 | 1.0 | 1.0 | 1.0 | 1.0 | 1.0 | 1.0 | 1.0 |
| Stearyl alcohol | 24.0 | 23.5 | 23.0 | 22.5 | 21.5 | 19.0 | 16.0 | 12.0 |
| Water | 36.0 | 36.0 | 36.0 | 36.0 | 36.0 | 36.0 | 36.0 | 36.0 |
| Propylene glycol, PG | 12.0 | 12.0 | 12.0 | 12.0 | 12.0 | 12.0 | 12.0 | 12.0 |
| Oleyl alcohol, OA | | 0.5 | 1 | 1.5 | 2.5 | 5.0 | 8.0 | 12.0 |
| Total | 100.0 | 100.0 | 100.0 | 100.0 | 100.0 | 100.0 | 100.0 | 100.0 |

The compositions were tested for release rate in Franz cells, where the drug release over silicone membranes was determined at 37° C. (Table 3b).

TABLE 3b

| | 9 | 10 | 11 | 12 | 13 | 14 | 15 | 16 |
|---|---|---|---|---|---|---|---|---|
| Cumulative amount, μg/cm² (6 h) | 126 | 169 | 175 | 200 | 235 | 255 | 246 | 207 |

Composition 14, comprising an approximate ratio in stiffening agent to release modifier of 4:1, produced an optimum drug release from the vehicle. The drug release was improved by 100 percent from addition of the release modifier (c.f. composition 9).

Example 4

A series of related creams were manufactured containing a biologically active agent (amlodipine), a release modifier (oleyl alcohol), a stiffening agent (stearyl alcohol), a polar solvent (propylene glycol), water and a petroleum fraction (petrolatum) as texture modifier (Compositions 13, 17 and 18, Table 4a).

TABLE 4a

| Composition, % (w/w) | 17 | 13 | 18 |
|---|---|---|---|
| Amlodipine base | 0.45 | 2.0 | 3.0 |
| Petrolatum, white | 26.0 | 25.0 | 25.0 |
| Tween 80 | 1.0 | 1.0 | 1.0 |
| Stearyl alcohol | 22.05 | 21.5 | 20.5 |
| Water | 36.0 | 36.0 | 36.0 |
| Propylene glycol, PG | 12.0 | 12.0 | 12.0 |
| Oleyl alcohol, OA | 2.5 | 2.5 | 2.5 |
| Total | 100.0 | 100.0 | 100.0 |

The compositions were tested for release rate in Franz cells, where the drug release over silicone membranes was determined at 37° C. (Table 4b).

TABLE 4b

| | 17 | 13 | 18 |
|---|---|---|---|
| Cumulative amount, μg/cm² (6 h) | 53 | 235 | 192 |

Compositions 13 and 18 provided superior drug flux.

Example 5

A series of related creams were manufactured containing a biologically active agent (amlodipine), a release modifier (oleyl alcohol), a stiffening agent (stearyl alcohol), a polar solvent (propylene glycol), water (or a substitute thereof) and a petroleum fraction (petrolatum) as texture modifier, to evaluate the effect of changing the amount of the polar solvent present, as well as to attempt to replace water with a buffer, glycerol or ethanol (Compositions 13 and 19-24, Table 5a).

TABLE 5a

| | Composition, % (w/w) | | | | | | |
|---|---|---|---|---|---|---|---|
| | 19 | 20 | 13 | 21 | 22 | 23 | 24 |
| Amlodipine base | 2.0 | 2.0 | 2.0 | 2.0 | 2.0 | 2.0 | 2.0 |
| Petrolatum, white | 25.0 | 25.0 | 25.0 | 25.0 | 25.0 | 25.0 | 25.0 |
| Tween 80 | 1.0 | 1.0 | 1.0 | 1.0 | 1.0 | 1.0 | 1.0 |
| Stearyl alcohol | 21.5 | 21.5 | 21.5 | 21.5 | 21.5 | 21.5 | 21.5 |
| Water | 40.0 | | 36.0 | | | | 30.0 |
| 0.1 M buffer, pH 7 | | | | 36.0 | | | |
| Glycerol | | 40.0 | | | 36.0 | | |
| Ethanol | | | | | | 36.0 | |
| Propylene glycol, PG | 8.0 | 8.0 | 12.0 | 12.0 | 12.0 | 12.0 | 18.0 |
| Oleyl alcohol, OA | 2.5 | 2.5 | 2.5 | 2.5 | 2.5 | 2.5 | 2.5 |
| Total | 100.0 | 100.0 | 100.0 | 100.0 | 100.0 | 100.0 | 100.0 |

The compositions were tested for release rate in Franz cells, where the drug release over silicone membranes was determined at 37° C. (Table 5b).

TABLE 5b

| | 19 | 20 | 13 | 21 | 22 | 23 | 24 |
|---|---|---|---|---|---|---|---|
| Cumulative amount, μg/cm² (6 h) | 173 | 162 | 235 | 188 | 230 | 248 | 144 |

Compositions 13, 22 and 23, comprising 12% propylene glycol, provided superior drug flux, and it was found that water may be replaced with glycerol or ethanol.

Example 6

A series of related creams were manufactured containing a biologically active agent (amlodipine), a release modifier (oleyl alcohol, or a substitute thereof), a stiffening agent (stearyl alcohol), a polar solvent (propylene glycol), water and a petroleum fraction (petrolatum) as texture modifier, to evaluate the effect of alternative tentative release modifiers (Compositions 13 and 25-29, Table 6a).

TABLE 6a

| | Composition, % (w/w) | | | | | |
|---|---|---|---|---|---|---|
| | 13 | 25 | 26 | 27 | 28 | 29 |
| Amlodipine base | 2.0 | 2.0 | 2.0 | 2.0 | 2.0 | 2.0 |
| Petrolatum, white | 25.0 | 25.0 | 25.0 | 25.0 | 25.0 | 25.0 |
| Tween 80 | 1.0 | 1.0 | 1.0 | 1.0 | 1.0 | 1.0 |
| Stearyl alcohol | 21.5 | 21.5 | 21.5 | 21.5 | 21.5 | 21.5 |
| Water | 36.0 | 36.0 | 36.0 | 36.0 | 36.0 | 36.0 |
| Propylene glycol, PG | 12.0 | 12.0 | 12.0 | 12.0 | 12.0 | 12.0 |
| Oleyl alcohol, OA | 2.5 | — | — | — | — | — |
| Lauric acid | — | 2.5 | — | — | — | — |
| Castor oil | — | — | 2.5 | — | — | — |
| Tetradecanol | — | — | — | 2.5 | — | — |
| Glyceryl monooleate | — | — | — | — | 2.5 | — |
| Oleic acid | — | — | — | — | — | 2.5 |
| Total | 100.0 | 100.0 | 100.0 | 100.0 | 100.0 | 100.0 |

The compositions were tested for release rate in Franz cells, where the drug release over silicone membranes was determined at 37° C. (Table 6b).

TABLE 6b

| | 13 | 25 | 26 | 27 | 28 | 29 |
|---|---|---|---|---|---|---|
| Cumulative amount, μg/cm² (6 h) | 235 | 2 | 143 | 154 | 181 | 2 |

Composition 13, comprising oleyl alcohol as release modifier provided superior drug flux, while fatty acids (lauric acid and oleic acid, compositions 25 and 29) decreased the drug release.

The invention claimed is:

1. A topical composition consisting essentially of:
as an active ingredient a dihydropyridine calcium antagonist and optionally a salt of the dihydropyridine calcium antagonist, wherein 10% or more of the dihydropyridine antagonist is present in uncharged form; and
a pharmaceutically acceptable carrier consisting essentially of
at least one stiffening agent selected from the group consisting of cetyl alcohol, stearyl alcohol, cetostearyl alcohol, eicosanol, docosanol, sorbitane monopalmitate, sorbitane monostearate, glyceryl monopalmitate, glyceryl monostearate, or glyceryl monopalmitostearate; and
at least one release modifier selected from the group consisting of dodecanol, tetradecanol, palmitoyl alcohol, oleyl alcohol, linoleyl alcohol, polyoxyethylene lauryl ether, polyoxyethylene myristyl ether, polyoxyethylene cetyl ether, polyoxyethylene stearyl ether, sorbitane monolaurate, sorbitane monooleate, or glyceryl monooleate, wherein the stiffening agent is present in an amount of 10 to 30% by weight and the release modifier is present in an amount of 1 to 15% by weight, the weight % being based on the total weight of the composition.

2. The composition according to claim 1, wherein the dihydropyridine calcium antagonist is present in the free base form.

3. The composition according to claim 1, wherein the dihydropyridine calcium antagonist is amlodipine, felodipine, lacidipine, nitrendipine, or nisoldipine.

4. The composition according to claim 1, wherein the stiffening agent is cetyl alcohol, stearyl alcohol, or cetostearyl alcohol.

5. The composition according to claim 1, wherein the release modifier is dodecanol, tetradecanol, palmitoyl alcohol, oleyl alcohol, linoleyl alcohol, or glyceryl monooleate.

6. The composition according to claim 1, wherein the release modifier is dodecanol, tetradecanol, palmitoyl alcohol, oleyl alcohol, or linoleyl alcohol.

7. A topical composition consisting essentially of:
as an active ingredient a dihydropyridine calcium antagonist and optionally a salt of the dihydropyridine calcium antagonist, wherein 10% or more of the dihydropyridine antagonist is present in uncharged form; and
a pharmaceutically acceptable carrier consisting essentially of
at least one stiffening agent selected from the group consisting of cetyl alcohol, stearyl alcohol, cetostearyl alcohol, eicosanol, docosanol, sorbitane monopalmitate, sorbitane monostearate, glyceryl monopalmitate, glyceryl monostearate, or glyceryl monopalmitostearate;
at least one release modifier selected from the group consisting of dodecanol, tetradecanol, palmitoyl alcohol, oleyl alcohol, linoleyl alcohol, polyoxyethylene lauryl ether, polyoxyethylene myristyl ether, polyoxyethylene cetyl ether, polyoxyethylene stearyl ether, sorbitane monolaurate, sorbitane monooleate, or glyceryl monooleate, wherein the stiffening agent is present in an amount of 10 to 30% by weight and the release modifier is present in an amount of 1 to 15% by weight, the weight % being based on the total weight of the composition; and
a polar solvent having an octanol-water partition coefficient (P) of $-1.5 < \log P < 0.5$.

8. The composition according to claim 7, wherein the polar solvent is diethanol amine, dipropylene glycol, diethylene glycol monoethyl ether, methyl ethyl ketone, 1-methyl-2-pyrrolidone, 1-propanol, 2-propanol, propylene glycol, or propylene carbonate, or a combination thereof; preferably diethylene glycol monoethyl ether, 1-methyl-2-pyrrolidone, propylene glycol, or propylene carbonate, or a combination thereof, more preferably propylene glycol.

9. The composition according to claim 7, wherein the polar solvent is present in an amount of up to 20% by weight, based on the weight of the composition.

10. The composition according to claim 1, further consisting essentially of 15 to 75% by weight of a petroleum fraction, based on the weight of the composition.

11. A composition according to claim 10, wherein the stiffening agent and the release modifier are present in a weight ratio of 10:1 to 1:1.

12. A method of treating a dermal or mucosal disorder, which comprises administering to a patient in need of such treatment the composition as defined in claim 1 in a therapeutically effective amount.

13. The method according to claim 12, wherein the disorder is acute anal fissures, chronic anal fissures, or hemorrhoids.

14. The method according to claim 12, wherein the composition is administered topically in or around the anal canal.

15. The composition according to claim 1, wherein the dihydropyridine calcium antagonist is present in an amount of up to 6% by weight based on the weight of the composition.

16. The composition according to claim 1, wherein the dihydropyridine calcium antagonist is present in an amount of 0.1 to 3% by weight based on the weight of the composition.

17. A topical composition for treatment of a dermal or mucosal disorder consisting essentially of:
as an active ingredient a dihydropyridine calcium antagonist or a salt of the dihydropyridine calcium antagonist; and
a pharmaceutically acceptable carrier consisting essentially of:
at least one stiffening agent selected from the group consisting of cetyl alcohol, stearyl alcohol, cetostearyl alcohol, eicosanol, docosanol, sorbitane monopalmitate, sorbitane monostearate, glyceryl monopalmitate, glyceryl monostearate, or glyceryl monopalmitostearate; and
at least one release modifier selected from the group consisting of dodecanol, tetradecanol, palmitoyl alcohol, oleyl alcohol, linoleyl alcohol, polyoxyethylene lauryl ether, polyoxyethylene myristyl ether, polyoxyethylene cetyl ether, polyoxyethylene stearyl ether, sorbitane monolaurate, sorbitane monooleate, or glyceryl monooleate, wherein the stiffening agent is present in an amount of 10 to 30% by weight and the release modifier is present in an amount of 1 to 15% by weight, the weight % being based on the total weight of the composition.

18. A topical composition for treatment of a dermal or mucosal disorder consisting essentially of:
   as an active ingredient a dihydropyridine calcium antagonist or a salt of the dihydropyridine calcium antagonist; and
   a pharmaceutically acceptable carrier consisting essentially of:
      at least one stiffening agent selected from the group consisting of stearyl alcohol or glyceryl monostearate; and
   a release modifier consisting essentially of oleyl alcohol, wherein the stiffening agent is present in an amount of 10 to 30% by weight and the release modifier is present in an amount of 1 to 15% by weight, the weight % being based on the total weight of the composition.

* * * * *